US008900155B2

(12) United States Patent
Zhen et al.

(10) Patent No.: US 8,900,155 B2
(45) Date of Patent: Dec. 2, 2014

(54) NON-INVASIVE BLOOD PRESSURE MONITORING SYSTEM

(75) Inventors: Ken Zhen, Lincoln, MA (US); Clifford M. Risher-Kelly, Wells, ME (US)

(73) Assignee: Draeger Medical Systems, Inc., Andover, MA (US)

( * ) Notice: Subject to any disclaimer, the term of this patent is extended or adjusted under 35 U.S.C. 154(b) by 1402 days.

(21) Appl. No.: 12/446,270

(22) PCT Filed: Nov. 9, 2007

(86) PCT No.: PCT/US2007/084264
§ 371 (c)(1),
(2), (4) Date: Apr. 20, 2009

(87) PCT Pub. No.: WO2008/061005
PCT Pub. Date: May 22, 2008

(65) Prior Publication Data
US 2010/0298723 A1   Nov. 25, 2010

Related U.S. Application Data

(60) Provisional application No. 60/865,187, filed on Nov. 10, 2006.

(51) Int. Cl.
*A61B 5/02*      (2006.01)
*A61B 5/022*     (2006.01)
*A61B 5/021*     (2006.01)

(52) U.S. Cl.
CPC ............. *A61B 5/022* (2013.01); *A61B 5/02141* (2013.01)
USPC ................................ 600/490; 60/481; 60/485

(58) Field of Classification Search
USPC .................................................. 600/485, 490
See application file for complete search history.

(56) References Cited

U.S. PATENT DOCUMENTS

| 4,178,918 | A   |   | 12/1979 | Cornwell |         |
|-----------|-----|---|---------|----------|---------|
| 4,800,892 | A   | * | 1/1989  | Perry et al. | 600/490 |
| 4,898,180 | A   | * | 2/1990  | Farrelly et al. | 600/494 |
| 5,692,512 | A   | * | 12/1997 | Flachslaender | 600/490 |
| 5,740,001 | A   |   | 4/1998  | Flachslaender et al. |         |
| 5,850,334 | A   |   | 12/1998 | Flachslaender |         |
| 6,175,752 | B1  | * | 1/2001  | Say et al. | 600/345 |
| 6,344,025 | B1  | * | 2/2002  | Inagaki et al. | 600/490 |
| 2002/0107476 | A1 | * | 8/2002 | Mann et al. | 604/67 |
| 2007/0282208 | A1 | * | 12/2007 | Jacobs et al. | 600/485 |

FOREIGN PATENT DOCUMENTS

EP             0 769 266        4/1997

* cited by examiner

*Primary Examiner* — Michael D'Angelo
(74) *Attorney, Agent, or Firm* — DLA Piper LLP (US)

(57) ABSTRACT

A non-invasive blood pressure monitoring system, includes an air channel having one or more inlet and exhaust ports to ambient air. An electronically controlled pump inflates and deflates a cuff applied to a patient limb with air via the air channel. A water tight sealed housing containing electronic circuitry for processing signals used in deriving a measurement of patient blood pressure in conjunction with inflating and deflating the cuff. The water tight sealed housing also is sealed from the air channel.

18 Claims, 4 Drawing Sheets

NON-INVASIVE BLOOD PRESSURE MONITORING SYSTEM

FIELD OF THE INVENTION

The present invention relates to a non-invasive blood pressure (NiBP) monitoring system, and in particular to an automatic NiBP monitoring system which may be used in an environment subject to moisture and/or other contaminants in the ambient air.

BACKGROUND OF THE INVENTION

Non-invasive blood pressure (NiBP) monitoring is a non-invasive means of assessing a patient's circulatory and cardiovascular status. The ejection of blood from the left side of the heart initiates a pressure wave that precedes the actual flow of blood. The wave of pulsating blood causes turbulence and vibrations of the blood vessel walls. With an inflatable cuff applied to patient's limb (arm or leg), an NiBP monitor measures a patient's arterial blood pressure by detecting these arterial wall vibrations, which are known as Korotkoff signals.

An automatic NiBP monitoring system comprises a cuff, air pump, valves, pressure sensors, and hoses, typically contained in an enclosure. The air pump compresses the air and inflates the cuff. Valves control the inflation and deflation of the cuff. Control electronics control the operation of the pump and valves, receive signals from the pressure sensors, and calculate the blood pressure from these signals.

Traditionally an automatic NiBP monitoring system takes the air used for inflating the cuff in through the enclosure which has a port to the ambient air. When the cuff is deflated, the air from the cuff is also vented through the enclosure to the port to the ambient air. This means that moisture and/or contaminants in the ambient air pass through the enclosure when the cuff is inflated, and then again when the cuff is deflated.

It is often desirable to monitor a patient's blood pressure while a patient is ambulatory. For such cases, a handheld or wearable NiBP monitoring system might be used. Electronics, such as the control electronics in an automatic NiBP monitoring system, are sensitive to the presence of water and/or other such contaminants, and may malfunction in their presence. A water proof or water resistant NiBP monitoring system is needed so that the patient may be monitored and still be able to perform normal functions such as showering, bathing, washing, etc. In such a system, it is also desirable that the air channel be cleanable so that contaminants which accumulate in the air channel may be removed to maintain the proper operation of the system.

BRIEF SUMMARY OF THE INVENTION

The inventor has realized that a water proof NiBP monitoring system or integrated patient monitoring system requires an air channel isolated from the enclosure or housing containing the control electronics.

In accordance with principles of the present invention, a non-invasive blood pressure monitoring system includes an air channel having one or more inlet and exhaust ports to ambient air. An electronically controlled pump inflates a cuff applied to a patient limb with air via the air channel. A water tight sealed housing contains electronic circuitry for processing signals used in deriving a measurement of patient blood pressure in conjunction with inflating and deflating the cuff. The water tight sealed housing also is sealed from the air channel.

In such a system, the separation of the air channel from the water tight sealed housing allows the air channel to be cleaned or flushed.

DETAILED DESCRIPTION OF THE INVENTION

Figure 1:
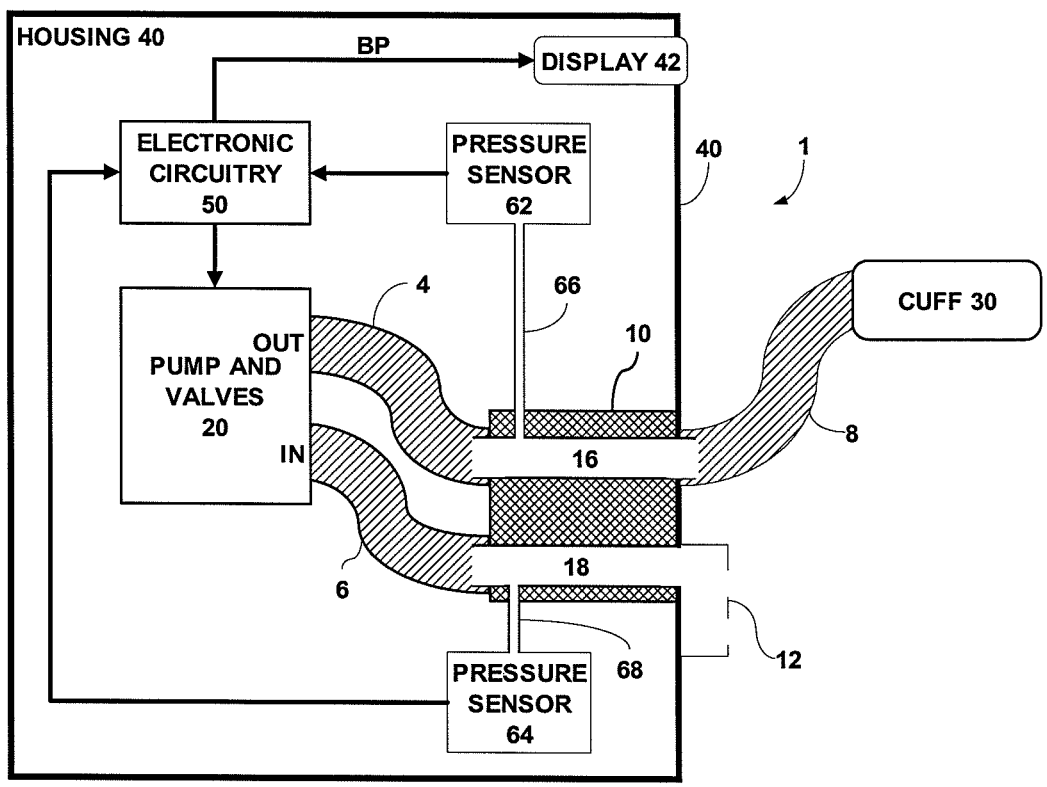
FIG. 1 is a diagram partially in block form and partially in schematic form of a non-invasive blood pressure monitoring system according to principles of the present invention.

FIG. 1 is a diagram partially in block form and partially in schematic form of a non-invasive blood pressure monitoring system 1 according to principles of the present invention. In FIG. 1, an air channel 10, has one or more inlet and exhaust ports 12 to ambient air. The air channel 10 has a first opening 18 which routes air from the inlet and exhaust ports 12 to an input port of an electronically controlled pump 20 via a tube or hose 6. A second opening 16 of the air channel 10 routes air from an output port of the electronically controlled pump 20 to a cuff 30 via tubes or hoses 4 and 8. The electronically controlled pump 20 inflates the cuff 30 applied to a patient limb via the air channel 10 in conjunction with electronically controlled valves attached to the pump 20. One skilled in the art understands that typically, the cuff 30 deflates by controlling the electronically controlled valves to connect the cuff 30 to the inlet and exhaust ports 12, allowing the air in the cuff 30 to pass back to the ambient air through the air channel 10. However, one skilled in the art further understands that the electronically controlled pump and valves 20 may be controlled so that the pump 20 actively pumps air out of the cuff 30 into the ambient air through the air channel 10 to the inlet and exhaust ports 12.

A water tight sealed housing 40 contains the pump and valves 20, and the electronic circuitry 50 for processing signals used in deriving a measurement of patient blood pressure in conjunction with inflating and deflating the cuff 30. The water tight sealed housing 40 is also sealed from the air channel 10. The water tight sealed housing 40 also contains a pair of pressure sensors 62 and 64 for sensing the pressure of the air in the respective openings 16 and 18 in the air channel 10 via tubes or hoses 66 and 68, respectively. The signals produced by the pressure sensors 62 and 64 are coupled to the electronic circuitry 50.

In operation, the inflatable cuff 30 is applied to a limb, e.g. an arm or leg, of a patient. The electronic circuitry 50 controls the electronically controlled pump and valves 20 to inflate the cuff 30 to the point where the peripheral blood flow is occluded, and then to deflate the cuff 30 to the point where blood flow returns. Signals from the pressure sensors 62 and 64, representing the pressure oscillations in the cuff 30 following return of blood flow, are analyzed by the electronic circuitry 50 to determine a systolic and a diastolic blood pressure measurement. The electronic circuitry 50 generates the BP (blood pressure) signal representing the systolic and diastolic blood pressure measurement. This technique is sometimes referred to as the oscillometry technique. Other techniques for performing an NiBP measurement also exist, such as auscultation, tonometry and volume-clamp techniques. The system 1 may be configured to utilize these, or other similar, techniques to produce blood pressure measurements in accordance with principles of the present invention. The signal BP is coupled to a display device 42, which displays the results of the blood pressure measurement.

In a system as illustrated in FIG. 1, the air channel 10 is capable of being flushed with: (a) air, and/or (b) a liquid. The air channel 10 exclusively acquires and expels air or fluid via the air channel 10 substantially without air or fluid leakage into the housing 40. That is, the air channel 10 is the exclusive pathway for air to pass from the ambient air to the cuff 30, and vice-versa; this air does not pass into or out of the inside of the housing 40. In one embodiment, the air channel 10 is a flattened channel having one cross-sectional dimension substantially greater than the other cross-sectional dimension, as described in more detail below.

The water tight sealed housing 40 contains electronic circuitry 50 for controlling the pump and valves 20, and for generating the BP signal representing the patient's blood pressure in response to pressure representative signals from the pressure sensors 62 and 64. In some embodiments, the water tight sealed housing 40 is sealed from the air channel 10 using a gasket, as described in detail below. The water tight sealed housing 40 may be fabricated so that it is capable of achieving an IPX7 international protection rating for the housing 40. An international protection (IP) rating, sometimes also referred to as an ingress protection rating, classifies a level of protection provided by a housing against the intrusion of external substances, e.g. water. An IPX7 rating specifies the degree of protection of equipment inside a housing against harmful ingress of water. More specifically, an IPX7 rating specifies that ingress of water in harmful quantity shall not be possible when the housing is immersed in water of up to 1 meter.

Figure 2:
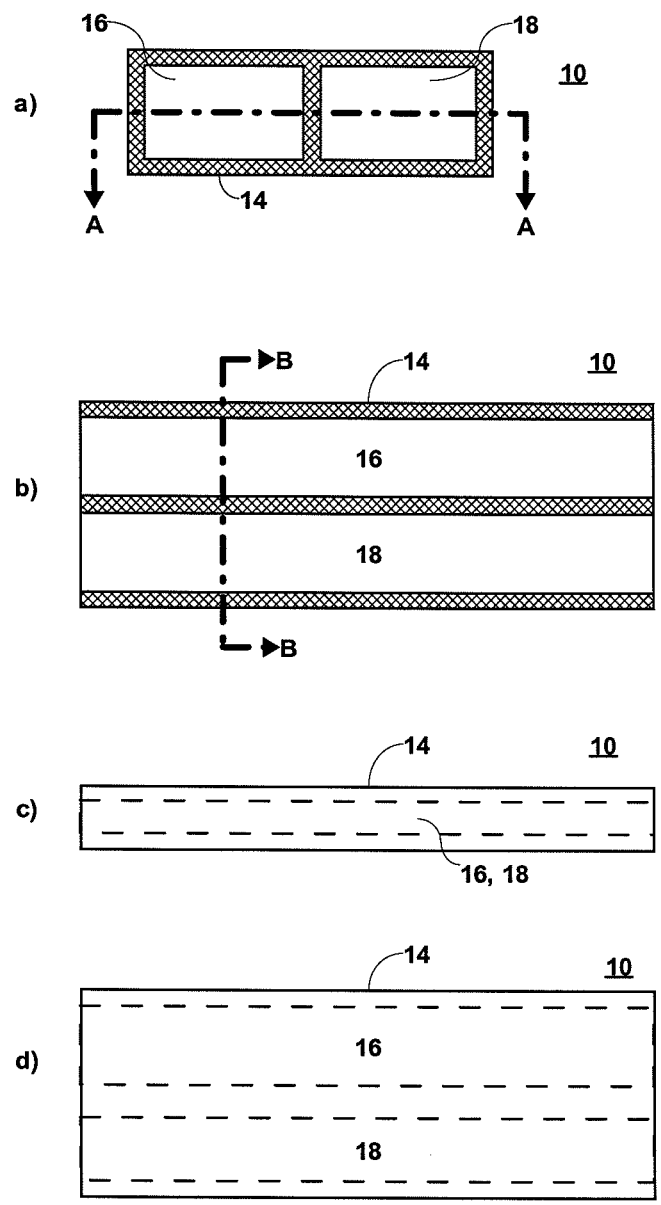
FIG. 2 is an orthogonal diagram illustrating an air channel according to principles of the present invention.

FIG. 2 is an orthogonal diagram illustrating an air channel 10 according to principles of the present invention. Referring concurrently to FIG. 2a and FIG. 2b, FIG. 2a is a transverse view along the B-B cross-section (of FIG. 2b), and FIG. 2b is a longitudinal view along the A-A cross-section (of FIG. 2a) of the air channel 10. The air channel 10 includes an enclosure 14 within which two elongated openings, 16 and 18 are formed. One of the openings, e.g. 18, routes air from the ambient outside air to the pump 20 (FIG. 1), and the other, e.g. 16, routes air from the pump 20 to the cuff 30. The air channel 10 illustrated in FIG. 2 is a flattened channel having one cross-sectional dimension, e.g. the horizontal dimension in FIG. 2a, substantially greater than the other cross-sectional dimension, e.g. the vertical dimension in FIG. 2a. FIG. 2c illustrates a side view, and FIG. 2d illustrates a top view of the air channel 10 with the openings 16 and 18 in the enclosure 14 illustrated by hidden (dashed) lines.

Figure 3:
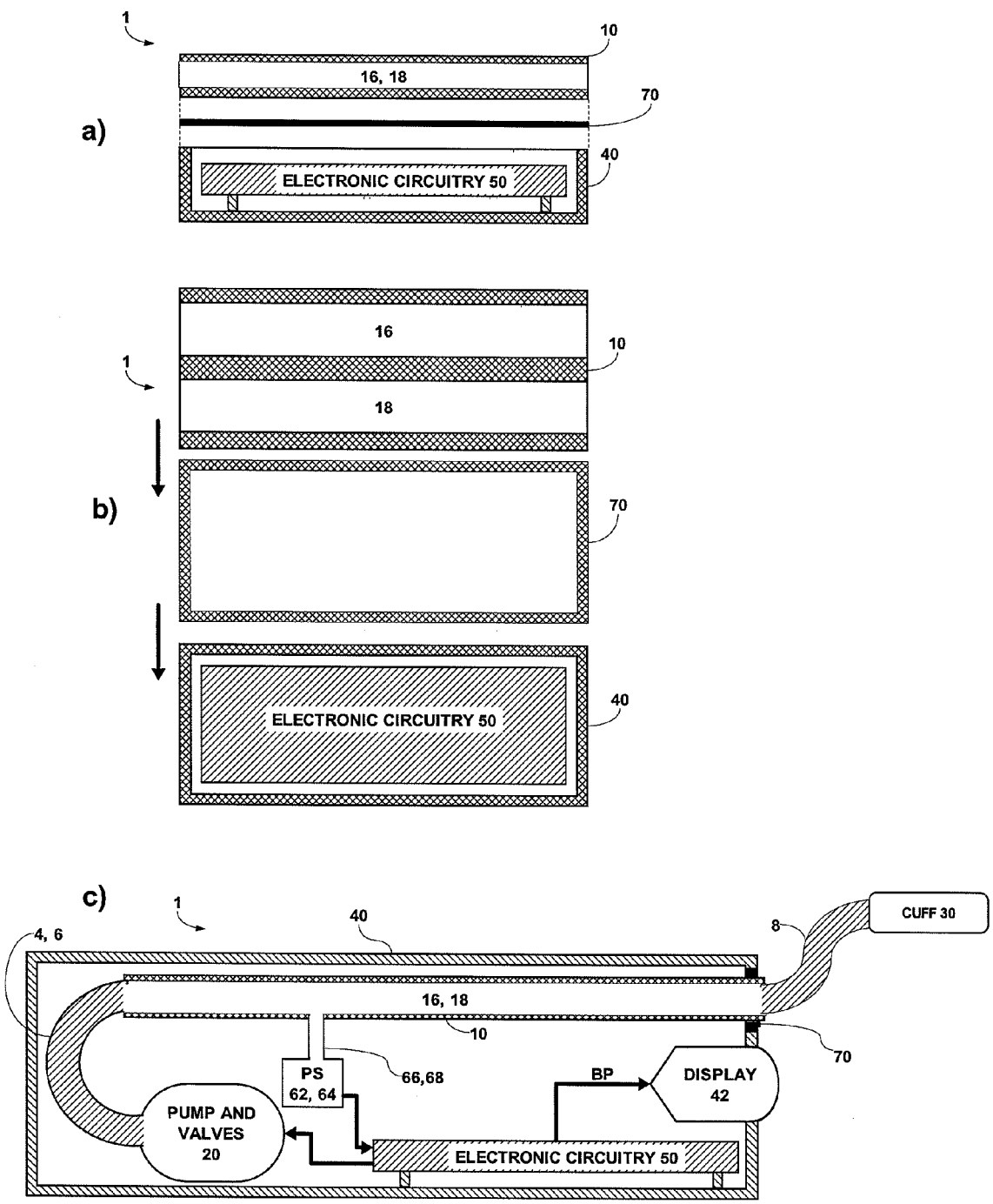
FIG. 3 is an assembly diagram of a non-invasive blood pressure monitoring system according to principles of the present invention.

FIG. 3 is an assembly diagram of a non-invasive blood pressure monitoring system 1 according to principles of the present invention. FIG. 3a is a side assembly view, FIG. 3b is a top assembly view and FIG. 3c is a more detailed side view of the system 1 as assembled. In FIG. 3a and FIG. 3b, the air channel 10, containing the openings 16 and 18, is aligned over the housing 40. The electronic circuitry 50 is mounted within the housing 40. A gasket 70 is installed between the air channel 10 and the housing 40 and aligned with the top edges of the housing 40. The gasket 70 forms a water proof seal between the air channel 10 and the housing 40, giving the enclosure an IPX7 international protection rating. The air channel 10 may be cleaned by being flushed with air and/or liquid. In some embodiments, the air channel 10 may be removed from the housing 40 to access the electronic circuitry 50. One skilled in the art recognizes that there are alternate ways, other than using a gasket, of sealing the housing 40.

FIG. 3c shows a more detailed side view of the non-invasive blood pressure monitoring system 1 as assembled. The electronic circuitry 50 provides control signals to the pump and valves 20 and receives sensor signals from the pressure sensors (PS) 62 and 64. The air channel 10 is connected to the pump and valves 20 via tubes or hoses 4 and 6, and to the cuff 30 via tube or hose 8. The place where the air channel 10 passes through the housing 40 is sealed with a gasket 70 to maintain the IPX7 rating.

As described above, the pump and valves 20 are controlled by the electronic circuitry 50 by signals provided from the electronic circuitry 50 to the pump and valves 20. Similarly pressure representative signals are supplied to the electronic circuitry 50 from the pressure sensors (PS) 62, 64. A signal BP representing the blood pressure measurement produced by the electronic circuitry 50 is supplied to the display device 42 which displays the results of the blood pressure measurements. The display device is viewable from outside of the housing 40, and maintains a seal between the inside and outside of the housing 40 to an IPX7 rating level. One skilled in the art understands that the system 1 may record the blood pressure measurement data for later study, and/or transmit it to remote monitoring equipment, in addition to or in place of, displaying the blood pressure measurement. In such a system, the signal BP is coupled to other circuitry (not shown) such as a recorder and/or transmitter.

Figure 4:
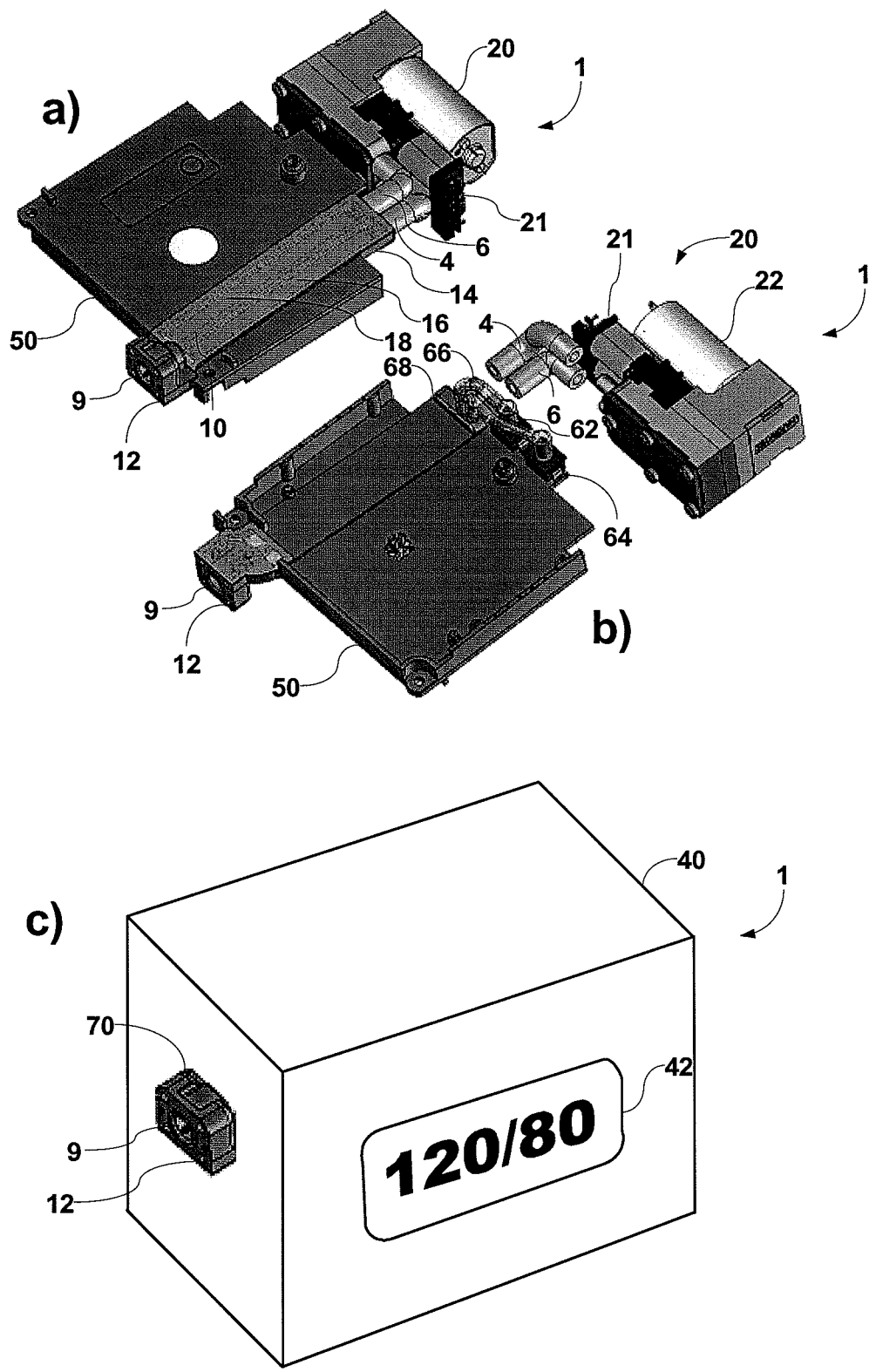
FIG. 4 is a more detailed isometric diagram illustrating a non-invasive blood pressure monitoring system according to principles of the present invention.

FIG. 4 is a more detailed isometric diagram illustrating a non-invasive blood pressure monitoring system 1 according to principles of the present invention. Those elements which are the same as those illustrated in FIG. 1 and FIG. 3 are designated by the same reference number and are not described in detail below. FIG. 4a is an isometric view of the top of a portion of the system 1 in an assembled state, and FIG. 4b is an isometric view of the bottom of the portion of the system 1 in a partially disassembled state. The portion of the system 1 illustrated in FIG. 4a and FIG. 4b is the portion which resides inside the housing 40 during normal operation.

Referring concurrently to FIG. 4a and FIG. 4b, the electronic circuitry 50 contains the electronic components (not shown) for performing the processing described above to provide blood pressure measurements. The air channel 10 is attached to the electronic circuitry 50 and includes inlet and exhaust port 12 and a port 9 attachable to the cuff 30. The inlet and exhaust port 12 includes four ports to the ambient air in the vicinity of the corners of the port 12. These ports are connected internally to opening 18 which connects those ports to an input port of the pump and valves 20 (in which the valves are illustrated as 21 and the pump is illustrated as 22) via tube or hose 6. The output port of the pump and valves 20 is connected to opening 16 via tube or hose 4. The opening 16 is connected to a port 9 located in the center of the inlet and exhaust port 12. A tube or hose 8 (not shown to simplify the figure) connected to a cuff 30 (also not shown) may be connected to the port 9. Pressure sensor 62 is coupled to opening 16 via a tube or hose 66 and pressure sensor 64 is coupled to opening 18 via a tube or hose 68.

FIG. 4c illustrates the housing 40 into which the assembly illustrated in FIG. 4a and FIG. 4b is inserted. The inlet and exhaust ports 12 and the cuff port 9 have access to the outside of the housing 40. The inlet and exhaust ports 12 receive and exhaust air to the outside ambient atmosphere, and the cuff port 9 connects to the cuff 30 (not shown) via a tube or hose 8 (also not shown). A gasket 70 is interposed between the inlet and exhaust ports 12 and cuff port 9 and the housing 40 to provide the IPX7 seal. A display device 42 is illustrated displaying the result of a blood pressure measurement. As described above, however, the system 1 may record blood pressure measurements for later study, or transmit them to a remote location, either instead of or in addition to displaying them on a display device 42.

The system 1 illustrated in FIG. 4 operates in the manner described above to generate a blood pressure measurement representative signal. When it is desired to clean the air channel 10, the air channel 10 is flushed with air or a liquid such as water or a disinfectant. The air channel 10 may be also removed from the housing 40 and cleaned. When clean, the air channel 10 may be reassembled with the housing 40 using a gasket 70, the tubes or hoses 4, 6, 8, 66 and 68 reconnected, and operation of the system 1 resumed.

The system 1 illustrated in the figures and described in detail above has been described in a particular configuration. One skilled in the art understands that any physical configuration may be fabricated in accordance with principles of the present invention using any suitable materials.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. A non-invasive blood pressure monitoring system, comprising:
    an air channel having one or more inlet and exhaust ports to ambient air;
    an electronically controlled pump for inflating a cuff applied to a patient limb with air acquired through the one or more inlet and exhaust ports of said air channel; and
    a water tight sealed housing containing the electronically controlled pump and electronic circuitry inside the housing for processing signals used in deriving a measurement of patient blood pressure in conjunction with inflating and deflating said cuff, the inside of said water tight sealed housing also being sealed from said air channel preventing air and liquid acquired or expelled through said air channel from leaking into the inside of the housing and contacting said electronic circuitry;
    wherein the one or more inlet and exhaust ports of said air channel and said electronically controlled pump are isolated from said electronic circuitry inside said water tight sealed housing and the seal between one or more inlet and exhaust ports of said air channel and said water tight sealed housing results in said air channel providing an exclusive pathway for air and liquid being passed to and expelled from the electronically controlled pump without air or liquid leakage into the housing.

2. The system according to claim 1, wherein said air channel is capable of being flushed with at least one of (a) air and (b) liquid.

3. The system according to claim 1, wherein said system is capable of achieving an IPX7 international protection rating for said housing.

4. The system according to claim 1, wherein said air channel exclusively acquires and expels air via said air channel substantially without air leakage into said housing.

5. The system according to claim 1, wherein said air channel is a flattened channel having one cross-sectional dimension substantially greater than an other cross-sectional dimension.

6. The system according to claim 1, wherein said water tight sealed housing contains electronic circuitry for controlling said pump.

7. The system according to claim 1, wherein said water tight sealed housing is sealed from said air channel using a gasket.

8. The system according to claim 1, wherein said air channel is selectively removeable.

9. A non-invasive blood pressure monitoring system, comprising:
    an electronically controlled pump for inflating and deflating a cuff applied to a patient limb with air via an air channel having one or more inlet and exhaust ports to ambient air;
    a water tight sealed housing containing the electronically controlled pump and electronic circuitry inside the housing for processing signals used in deriving a measurement of patient blood pressure in conjunction with inflating and deflating said cuff, the inside of said water tight sealed housing also being sealed from said air channel preventing air and liquid acquired or expelled through said air channel from leaking into the inside of the housing and contacting said electronic circuitry;
    wherein the seal between the one or more inlet and exhaust ports of said air channel and said water tight sealed housing results in said air channel providing an exclusive pathway for air and liquid being passed to and expelled from the electronically controlled pump without air or liquid leakage into the housing.

10. The system according to claim 9, wherein said air channel is capable of being flushed with at least one of (a) air and (b) liquid.

11. The system according to claim 9, wherein said system is capable of achieving an IPX7 international protection rating.

12. The system according to claim 9, wherein said air channel exclusively acquires and expels air via said air channel without air leakage into said housing.

13. The system according to claim 9, wherein said air channel is a flattened channel having one cross-sectional dimension substantially greater than the other cross-sectional dimension.

14. The system according to claim 9, wherein said water tight sealed housing contains electronic circuitry for controlling said pump.

15. The system according to claim 9, wherein said water tight sealed housing is sealed from said air channel using a gasket.

16. The system according to claim 9, wherein said air channel is selectively removeable.

17. A non-invasive blood pressure monitoring system, comprising:
    an air channel having one or more inlet and exhaust ports to ambient air;
    an electronically controlled pump for inflating and deflating a cuff applied to a patient limb with air acquired through the one or more inlet and exhaust ports of said air channel; and
    a water tight sealed housing containing the electronically controlled pump and electronic circuitry inside the housing for processing signals used in deriving a measurement of patient blood pressure in conjunction with inflating and deflating said cuff, the inside of said water tight sealed housing also being sealed from said air channel preventing air and liquid acquired or expelled through said air channel from leaking into the inside of the housing and contacting said electronic circuitry;

wherein the one or more inlet and exhaust ports of said air channel and said electronically controlled pump are isolated from said electronic circuitry inside said water tight sealed housing and the seal between one or more inlet and exhaust ports of said air channel and said water tight seal housing results in said air channel providing an exclusive pathway for air and liquid being passed to and expelled from the electronically controlled pump without air or liquid leakage into the housing.

18. The system according to claim 17, wherein said air channel is selectively removeable.

* * * * *